United States Patent
Assaf et al.

(10) Patent No.: US 9,788,753 B2
(45) Date of Patent: Oct. 17, 2017

(54) METHOD AND SYSTEM FOR CHARACTERIZING CORTICAL STRUCTURES

(75) Inventors: Yaniv Assaf, Tel-Aviv (IL); Daniel Barazany, Rishon-LeZion (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 715 days.

(21) Appl. No.: 12/712,306

(22) Filed: Feb. 25, 2010

(65) Prior Publication Data

US 2010/0215239 A1 Aug. 26, 2010

Related U.S. Application Data

(60) Provisional application No. 61/202,424, filed on Feb. 26, 2009.

(51) Int. Cl.
| | |
|---|---|
| *G06K 9/00* | (2006.01) |
| *A61B 5/055* | (2006.01) |
| *G06T 7/00* | (2017.01) |
| *A61B 5/00* | (2006.01) |

(52) U.S. Cl.
CPC ............ *A61B 5/055* (2013.01); *A61B 5/4064* (2013.01); *G06T 7/0012* (2013.01); *G06T 2207/10088* (2013.01); *G06T 2207/30016* (2013.01)

(58) Field of Classification Search
CPC . G06T 2207/10088; G06T 2207/30016; G06T 7/0012
USPC ........................................................ 382/121
See application file for complete search history.

(56) References Cited

U.S. PATENT DOCUMENTS

| | | | | |
|---|---|---|---|---|
| 7,795,867 | B2 * | 9/2010 | Eliav et al. ................... | 324/307 |
| 8,148,979 | B1 * | 4/2012 | Du .................. | 324/307 |
| 2003/0144587 | A1 * | 7/2003 | Ma ..................... | G01R 33/4838 |
| | | | | 600/410 |
| 2005/0240096 | A1 * | 10/2005 | Ackerman ............. | A61B 5/055 |
| | | | | 600/410 |
| 2006/0008517 | A1 * | 1/2006 | Lynch et al. .................. | 424/450 |
| 2007/0010732 | A1 * | 1/2007 | DeYoe ................ | A61B 5/4041 |
| | | | | 600/410 |
| 2007/0055151 | A1 * | 3/2007 | Shertukde et al. ........... | 600/437 |
| 2008/0091628 | A1 * | 4/2008 | Srinivasa et al. ............... | 706/12 |
| 2008/0287821 | A1 * | 11/2008 | Jung et al. .................... | 600/544 |
| 2008/0298653 | A1 * | 12/2008 | Amunts ................ | G06T 3/0093 |
| | | | | 382/128 |

OTHER PUBLICATIONS

Angenstein et al. "Manganese-Enhanced MRI Reveals Structural and Functional Changes in the Cortex of Bassoon Mutant Mice", Cerebral Cortex, 17: 28-36, Jan. 2007.

Barbier et al. "Imaging Cortical Anatomy by High-Resolution MR at 3.0T: Detection of the Stripe of Gennari in Visual Area 17", Magnetic Resonance in Medicine, 48: 735-738, 2002.

(Continued)

*Primary Examiner* — Reginald R Reyes

(57) ABSTRACT

A method of identifying brain structures is disclosed. The method comprises imaging the cortex of the brain via inversion recovery magnetic resonance imaging, such that at least two areas are zeroed in terms of their longitudinal relaxation times, and associating the two areas with different brain structures, thereby identifying brain structures.

29 Claims, 14 Drawing Sheets
(12 of 14 Drawing Sheet(s) Filed in Color)

(56) References Cited

OTHER PUBLICATIONS

Clark et al. "In Vivo Myeloarchitectonic Analysis of Human Striate and Extrastriate Cortex Using Magnetic Resonance Imaging", Cerebral Cortex, 2: 417-424, Sep./Oct. 1992.
Duyn et al. "High-Field MRI of Brain Cortical Substructure Based on Signal Phase", Proc. Natl. Acad. Sci. USA, 104(28): 11796-11801, Jul. 10, 2007.
Eickhoff et al. "High-Resolution MRI Reflects Mycloarchitecture and Cytoarchitecture of Human Cerebral Cortex", Human Brain Mapping, 24: 206-215, 2005.
Fatterpekar et al. "Cytoarchitecture of the Human Cerebral Cortex: MR Microscopy of Excised Specimens at 9.4 Tesla", AJNR, American Journal of Neuroradiology, 23: 1313-1321, Sep. 2002.
Hahn "An Accurate Nuclear Magnetic Resonance Method for Measuring Spin-Lattice Relaxation Times", Physical Review Letters, 76: 145-146, 1949.
Silva et al. "Detection of Cortical Laminar Architecture Using Manganese-Enhanced MRI", Journal of Neuroscience Methods, 167: 246-257, 2008.
Walters et al. "In Vivo Identification of Human Cortical Areas Using High-Resolution MRI: An Approach to Cerebral Structure-Function Correlation", Proc. Natl. Acad. Sci. USA, 100(5): 2981-2986, Mar. 4, 2003.
Yovel et al. "Virtual Definition of Neuronal Tissue by Cluster Analysis of Multi-Parametric Imaging (Virtual-Dot-Com Imaging)", NeuroImage, 35: 58-69, 2007.

\* cited by examiner

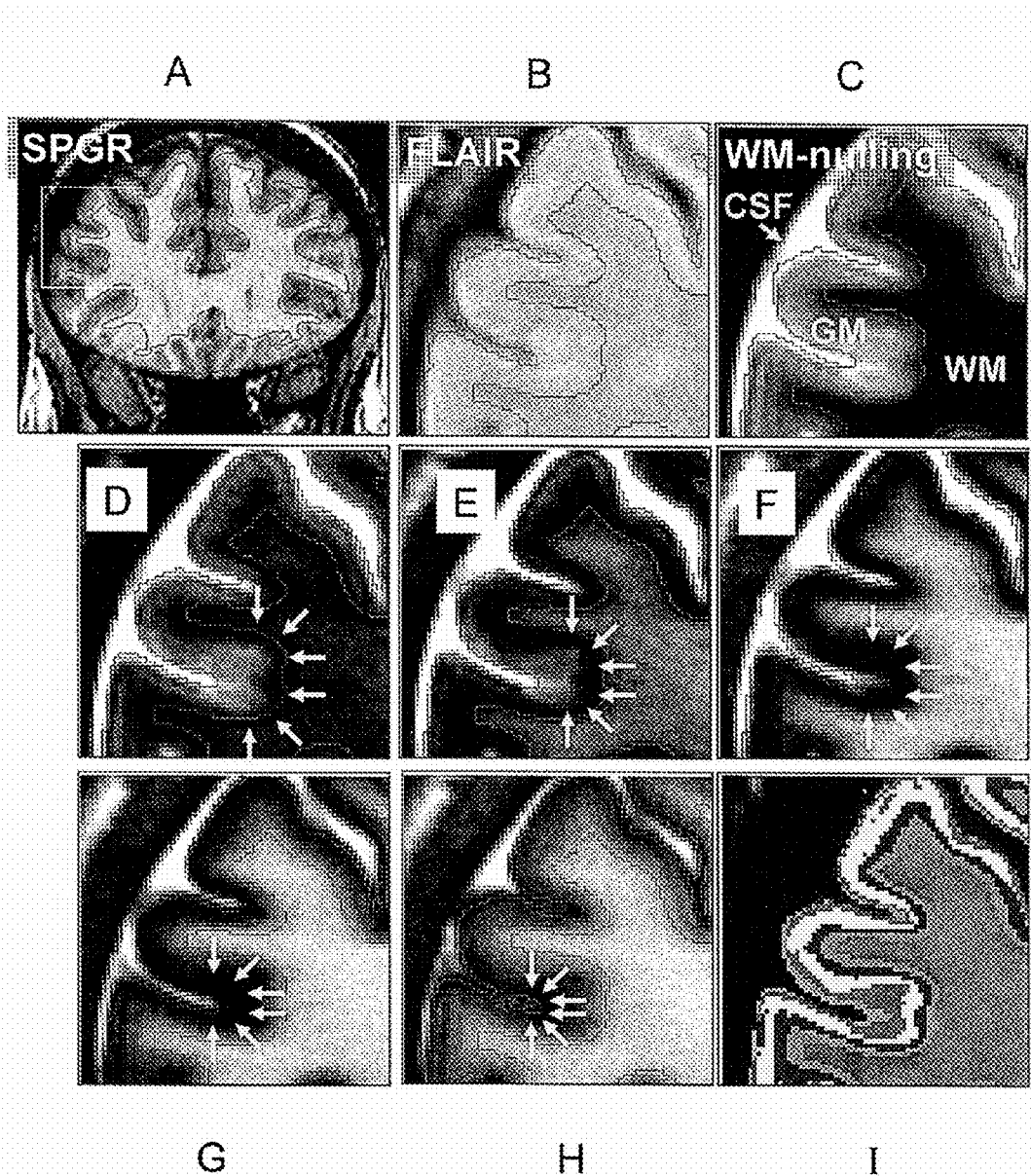
FIGS. 4A-I

FIG. 9B
FIG. 9E
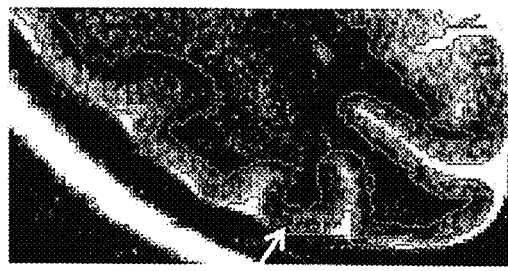
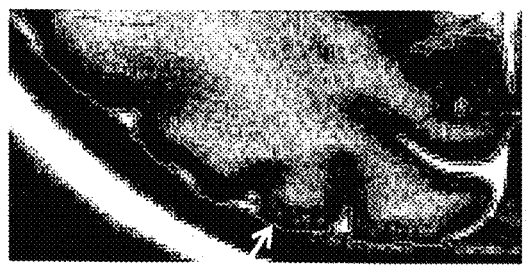
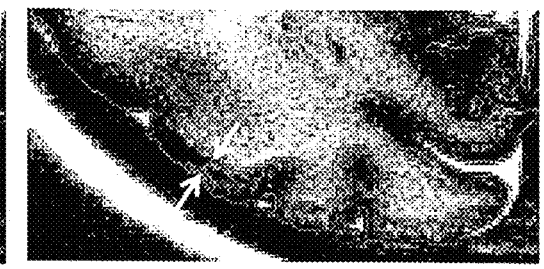
FIG. 9C
FIG. 9D
FIG. 9F
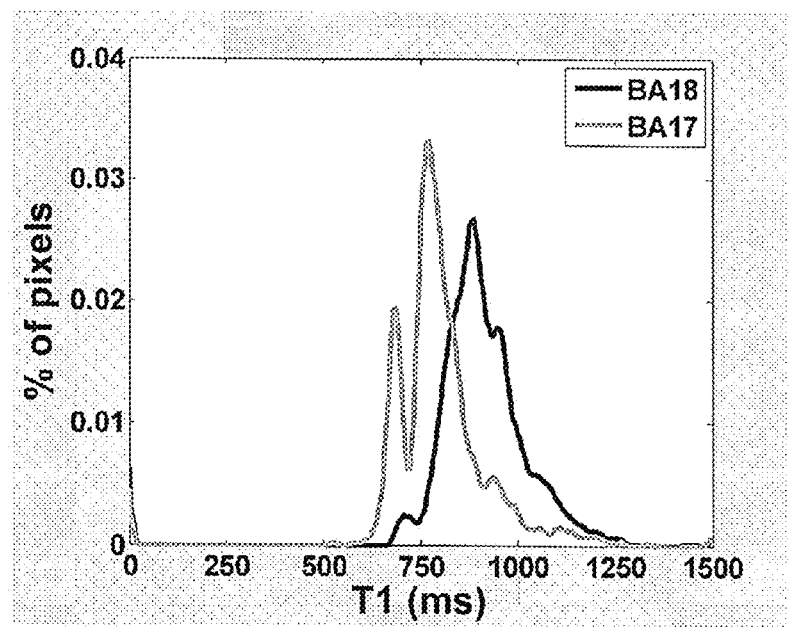

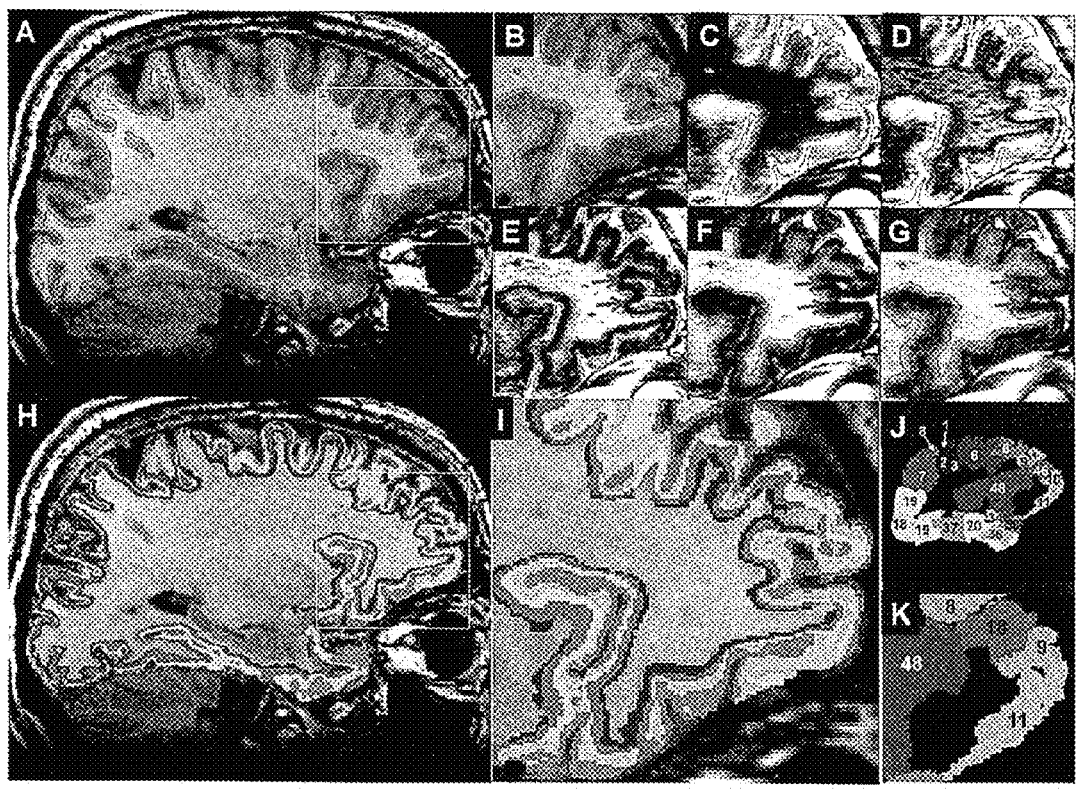
FIGS. 10A-K

METHOD AND SYSTEM FOR CHARACTERIZING CORTICAL STRUCTURES

RELATED APPLICATION/S

This application claims the benefit of priority from U.S. Provisional Patent Application No. 61/202,424 filed on Feb. 26, 2009, the contents of which are hereby incorporated by reference as if fully set forth herein.

FIELD AND BACKGROUND OF THE INVENTION

The present invention, in some embodiments thereof, relates to magnetic resonance imaging (MRI) and, more particularly, but not exclusively, to a method and system for presenting and optionally characterizing cortical structures.

The cortex is organized in a laminar arrangement of neuronal morphology (cortical layers), with six distinct layers of cellular arrangement having similar composition throughout the cortex but differ in width between regions. This morphological, cyto-architectonic feature of the cortex is the basis for its parcellation into neuro-anatomical regions. The most common reference of such parcellation is the Brodmann's map of 47 cortical regions introduced in 1907. Other cyto-architectonic based cortical segmentations exist, but Brodmann's parcellation is the most common brain localization system in neuroscience today.

The six cortical layers possess neurons with different composition and morphology. The density and shape of neurons greatly varies along the cortex; from scattered pattern of small neurons at the first layer (molecular layer) to dense pattern of large and small neurons and neuronal fibers at the deeper layers (pyramidal and multiform layers). In addition, each layer has characteristics connections with other layers or brain regions. For example, the inner-granular layer (layer IV), connects with the thalamus and other inter-hemispheric cortical regions.

The cortical layers are formed during development when neurons migrate to the cortex from the ventricular zone. The layers are formed such that the deepest layers are formed by newer neurons. The formation of the layers is synchronized with the formation of other brain structures that the specific layers connect with.

Several attempts have been made to identify brain structures in vivo. A quantitative comparison of the lamination patterns observed in high-resolution magnetic resonance (MR) images of the human cerebral cortex with both myelo- and cytoarchitectonic patterns has been reported in Eickhoff et al., 2005, "High-Resolution MRI Reflects Myeloarchitecture and Cytoarchitecture of Human Cerebral Cortex," Human Brain Mapping 24:206-215. This study has shown that the cortical lamination pattern visible on T1-weighted MR images reflects myelo- and cytoarchitecture.

U.S. Pat. No. 5,185,809 discloses a computerized technique for volumetric measurements of selected regions of the brain. The outline of a selected region in a slice of MR data is automatically determined and a volumetric measurement is made by determining for each slice the areas within the outline and summing the product of the areas and their respective thicknesses for all the slices.

U.S. Pat. No. 6,490,472 discloses a technique for producing an indication of the presence of Alzheimer's disease by measuring the functional connectivity at different locations in the brain. The technique involves measurement of functional connectivity of the brain between a plurality of locations in the hippocampus region of the brain that are affected by the disease. The measurement is made by acquiring MR images from a plurality of locations using an MRI system which includes an inversion recovery preparation sequence. The presence of the disease is determined when the measured connectivity is below a preset level.

Additional background art includes U.S. Pat. No. 5,588,431 and U.S. Published Application No. 20040162483.

SUMMARY OF THE INVENTION

According to an aspect of some embodiments of the present invention there is provided a method of identifying brain structures. The method comprises: imaging the cortex of the brain via inversion recovery magnetic resonance imaging, such that at least two areas are zeroed in terms of their longitudinal relaxation times; and associating the at least two areas with different brain structures, thereby identifying brain structures.

According to some embodiments of the invention the method further comprises analyzing images obtained by the magnetic resonance imaging so as to classify different regions of the cortex to a laminar pattern.

According to some embodiments of the invention the analysis comprises a multi-exponential signal decay fit.

According to some embodiments of the invention the magnetic resonance imaging is such that at least one of a white matter zone and a cerebrospinal fluid zone is zeroed in terms of its longitudinal relaxation time.

According to some embodiments of the invention the method further comprises identifying at least one Brodmann region among the at least two areas.

According to some embodiments of the invention the magnetic resonance imaging is at a resolution characterized by a unit voxel size of at least 1 cubic millimeter, or at least 4 cubic millimeters or at least 8 cubic millimeters.

According to some embodiments of the invention the method further comprises combining diffusion weighted magnetic resonance imaging with the inversion recovery magnetic resonance imaging.

According to some embodiments of the invention the method further comprises combining functional magnetic resonance imaging with the inversion recovery magnetic resonance imaging.

According to some embodiments of the invention the method further comprises identifying an abnormal laminar pattern in the cortex.

According to some embodiments of the invention the method further comprises associating the abnormal laminar pattern with a brain disease.

According to some embodiments of the invention the method further comprises treating the brain disease.

According to some embodiments of the invention the method further comprises repeating the imaging and the associating at different times for the same cortex so as to identify changes in a laminar pattern of the cortex.

According to some embodiments of the invention the method further comprises assessing brain plasticity based on the changes.

According to some embodiments of the invention the method further comprises assessing changes in brain function based on the changes in the laminar pattern.

According to an aspect of some embodiments of the present invention there is provided an apparatus for identifying brain structures. The apparatus comprises a processor configured for receiving inversion recovery magnetic resonance data describing the cortex of the brain in a manner such that at least two areas of the cortex are zeroed in terms of their longitudinal relaxation times, and processing the data such as to associating the at least two areas with different brain structures.

According to some embodiments of the invention the processor is configured for analyzing images obtained by the magnetic resonance imaging so as to classify different regions of the cortex to a laminar pattern.

According to some embodiments of the invention the processor is configured for performing a multi-exponential signal decay fit.

According to some embodiments of the invention the fit is performed along a vector perpendicular to the surface of the brain from a white matter region to a cerebrospinal fluid region.

According to some embodiments of the invention the analysis comprises three-dimensional analysis.

According to some embodiments of the invention the at least two areas comprises at least five laminar cortical layers, each corresponding to a different characteristic longitudinal relaxation time.

According to some embodiments of the invention the processor is configured for identifying at least one Brodmann region among the at least two areas.

According to some embodiments of the invention the processor is configured for combining diffusion weighted magnetic resonance imaging with the inversion recovery magnetic resonance imaging.

According to some embodiments of the invention the processor is configured for combining functional magnetic resonance imaging with the inversion recovery magnetic resonance imaging.

According to an aspect of some embodiments of the present invention there is provided a system for identifying brain structures. The system comprises a magnetic resonance imaging system configured for imaging the cortex of the brain via inversion recovery magnetic resonance imaging such that at least two areas of the cortex are zeroed in terms of their longitudinal relaxation times; and a processor configured for receiving inversion recovery magnetic resonance data from the magnetic resonance imaging system and processing the data such as to associating the at least two areas with different brain structures.

According to some embodiments of the invention the magnetic resonance imaging system is configured for imaging the cortex such that at least one of a white matter zone and a cerebrospinal fluid zone is zeroed in terms of its longitudinal relaxation time.

According to some embodiments of the invention the magnetic resonance imaging system is configured for imaging via diffusion weighted magnetic resonance imaging, wherein the processor is configured for combining the diffusion weighted magnetic resonance imaging with the inversion recovery magnetic resonance imaging.

According to some embodiments of the invention the magnetic resonance imaging system is configured for imaging via functional magnetic resonance imaging, wherein the processor is configured for combining the functional magnetic resonance imaging with the inversion recovery magnetic resonance imaging.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a flowchart diagram of a method suitable for identifying brain structures, according to various exemplary embodiments of the present invention;

FIG. 2 is a schematic illustration of a system for identifying brain structures, according to various exemplary embodiments of the present invention;

Figure 5A:
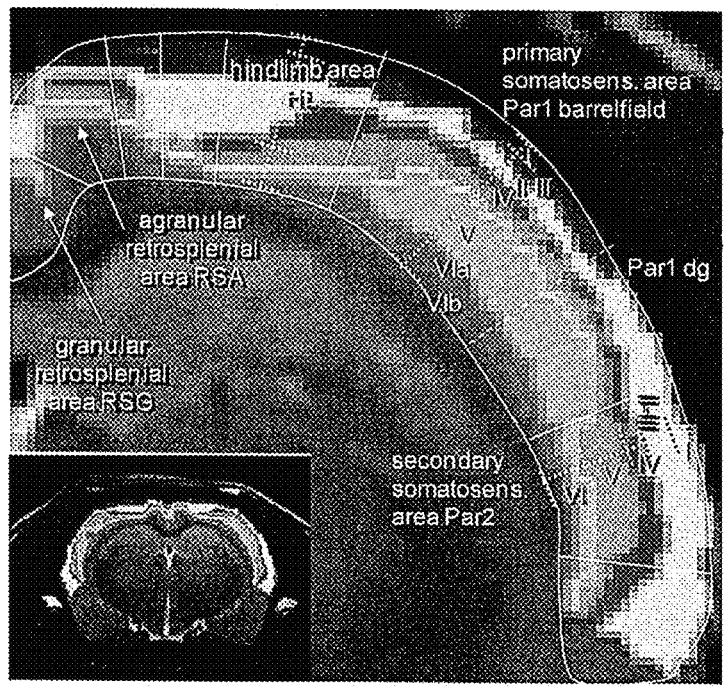
Figure 5B:
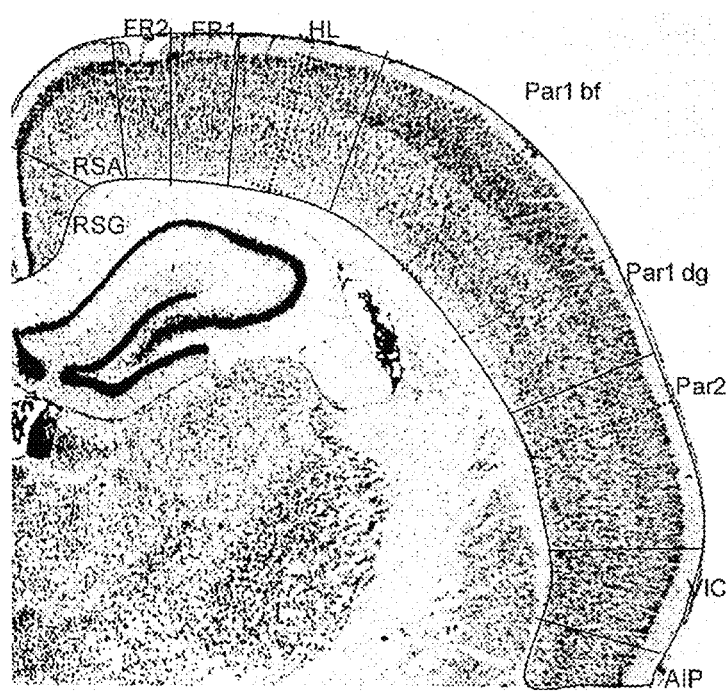
Figure 7A:
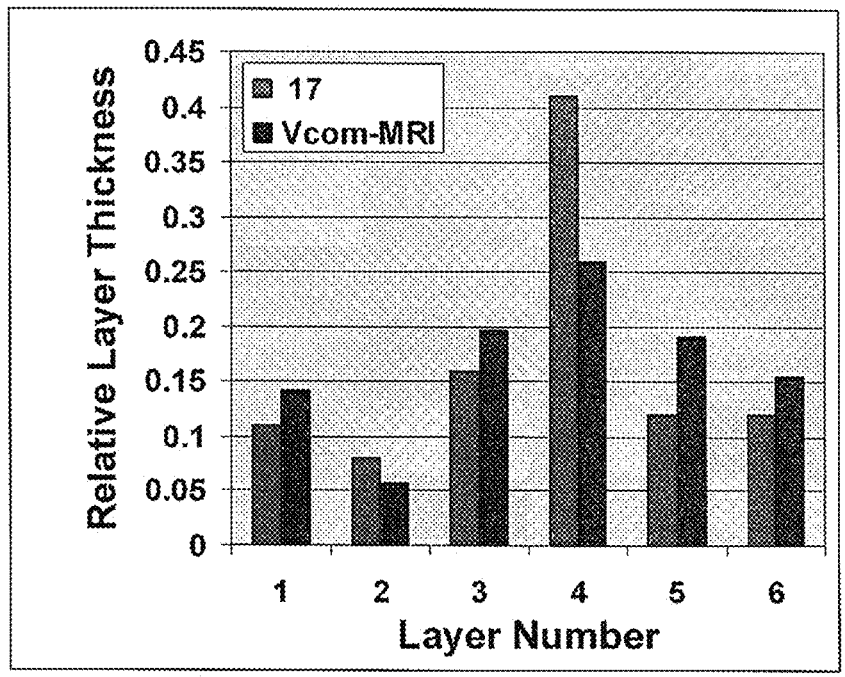
Figure 7B:
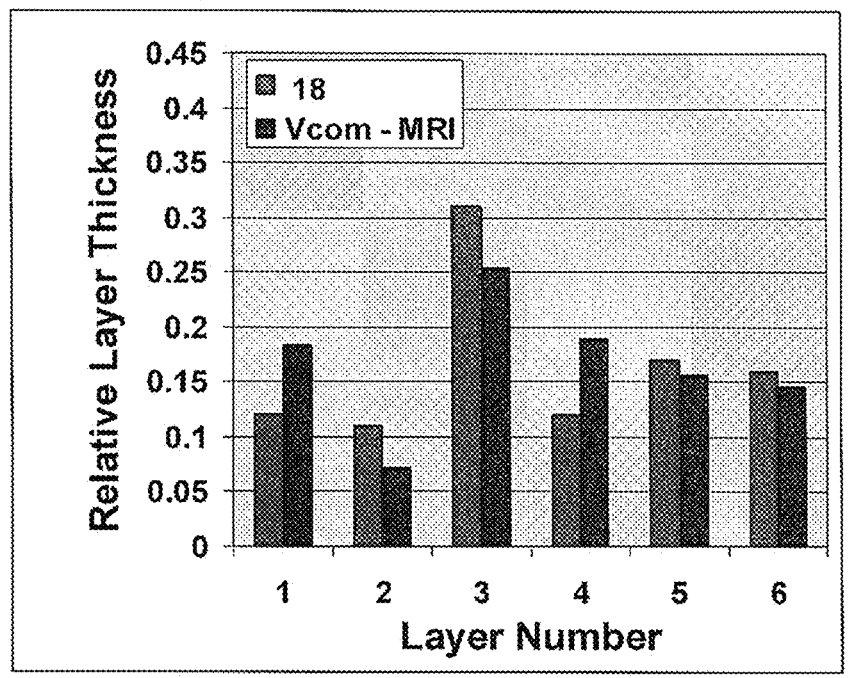
Figure 8:
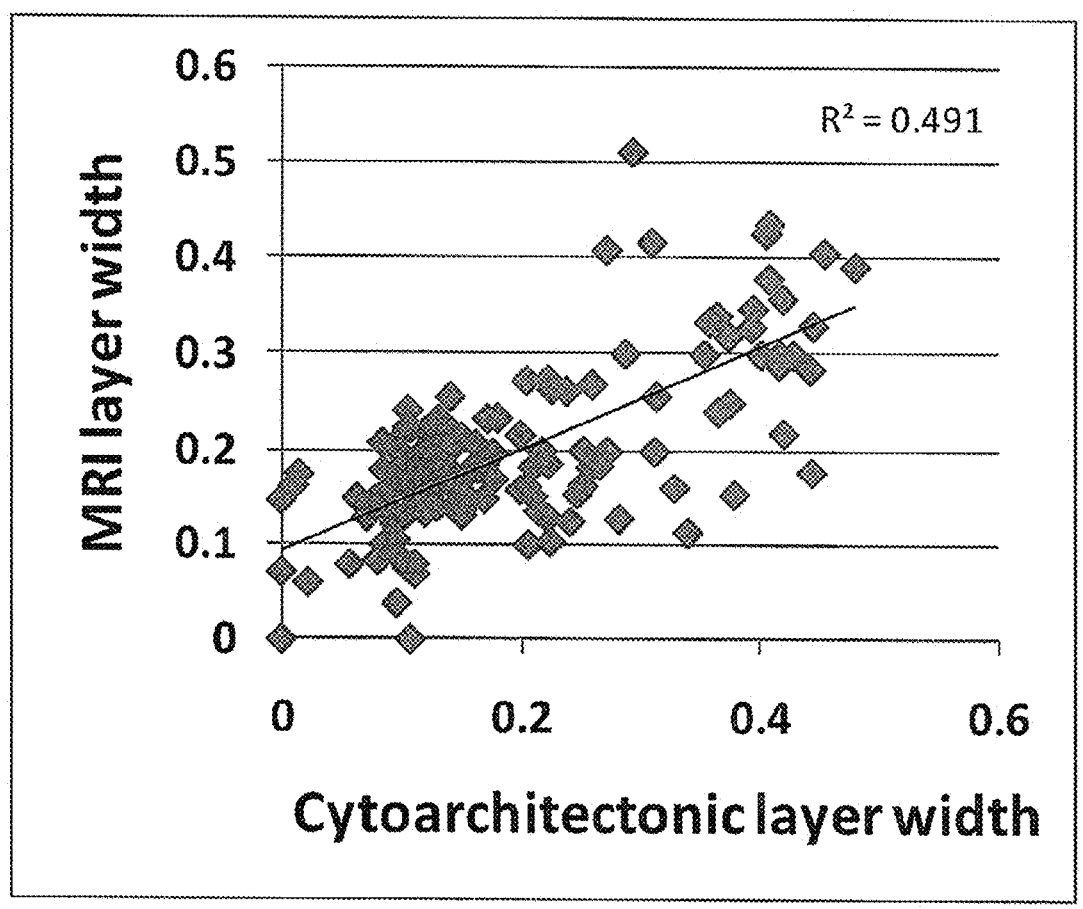
Figure 9A:
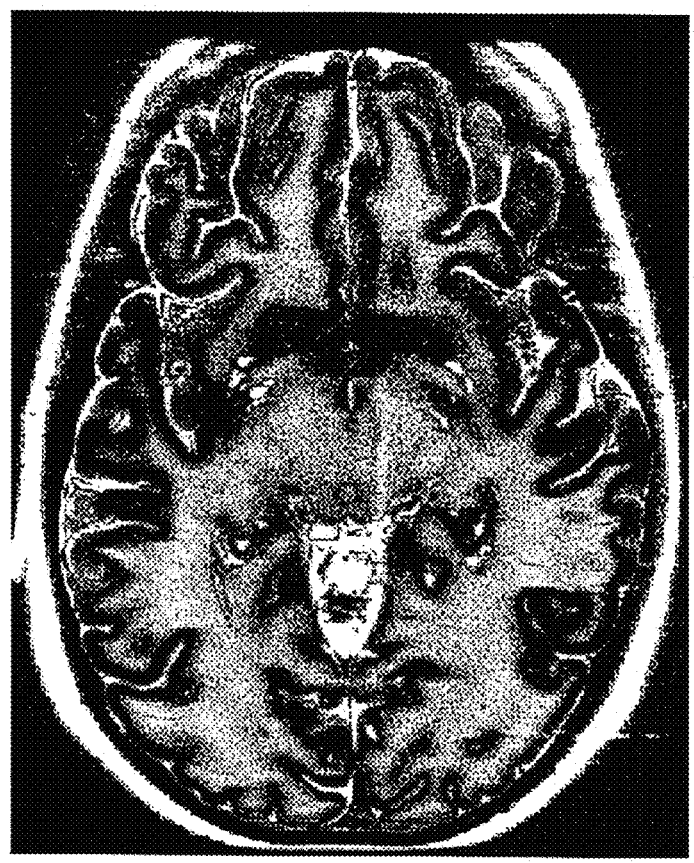
Figure 11:
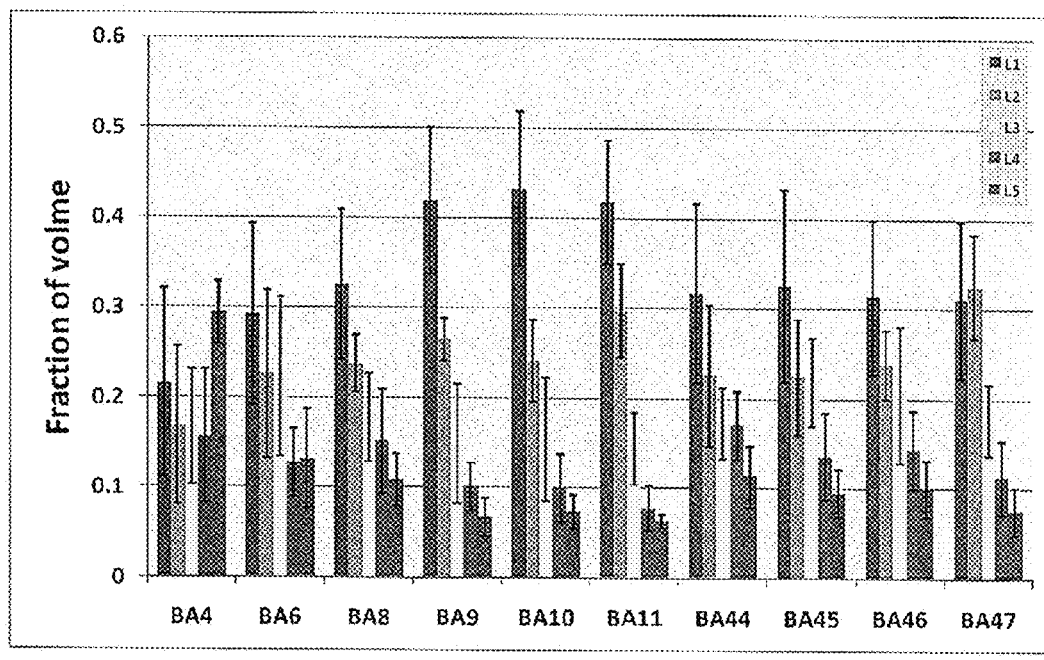
Figure 12:
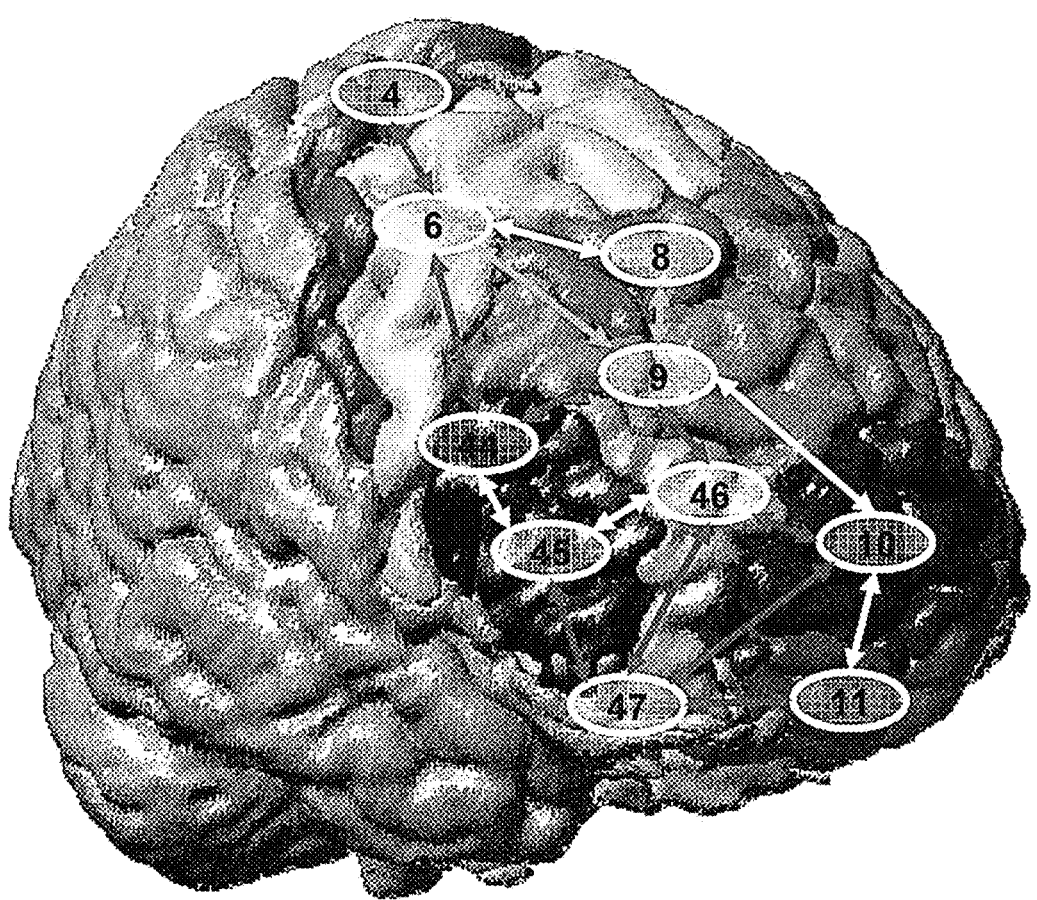

FIGS. 3A-E show histograms of inversion time and longitudinal relaxation time distributions across the entire cortex of a representative subject, as measured according to some embodiments of the present invention;

FIGS. 4A-C are SPGR-T1 (FIG. 4A), FLAIR (FIG. 4B) and inversion recovery (FIG. 4C) images, acquired according to some embodiments of the present invention;

FIGS. 4D-H are a series of inversion recovery images taken according to some embodiments of the present invention at various inversion times;

FIG. 4I shows results of multi-spectral cluster analysis of the dataset of FIGS. 4A-H, as obtained according to some embodiments of the present invention;

FIG. 5A shows cluster analysis of an inversion recovery dataset acquired in-vivo from a rat brain according to some embodiments of the present invention;

FIG. 5B shows cyto-architectonic analysis performed on histological sections of the brain shown in FIG. 5A;

FIGS. 6A-D show the difference in the lamination pattern between areas 17 and 18, as identified according to some embodiments of the present invention;

FIGS. 7A-B are charts showing a comparison between the lamination pattern as obtained by histology (red bars) and the analysis according to some embodiments of the present invention (blue bars) for Brodmann area (BA) 17 (FIG. 7A) and BA 18 (FIG. 7B);

FIG. 8 shows a comparison between the lamination pattern as obtained by histology (abscissa) and the analysis according to some embodiments of the present invention (ordinate) for 22 Brodmann areas;

FIGS. 9A-E shows inversion recovery MR analysis at different inversion times at the border between Brodmann area's 17 and 18, as obtained according to some embodiments of the present invention;

FIG. 9F shows histograms of longitudinal relaxation time distribution as calculated according to some embodiments of the present invention for the striate and ex-striate cortices;

FIGS. 10A-K show inversion recovery MR images of representative slice out of a three-dimensional dataset taken according to some embodiments of the present invention at different inversion times used in FIG. 9;

FIG. 11 shows the fraction of inversion recovery layers for the 10 Brodmann areas of the frontal lobe;

FIG. 12 shows a three-dimensional representation of a statistical and regional analysis of the frontal lobe inversion recovery layer fraction, as obtained according to some embodiments of the present invention.

DESCRIPTION OF SPECIFIC EMBODIMENTS OF THE INVENTION

The present invention, in some embodiments thereof, relates to magnetic resonance imaging (MRI) and, more particularly, but not exclusively, to a method and system for presenting and optionally characterizing cortical structures.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Magnetic Resonance Imaging (MRI) is a method to obtain an image representing the chemical and physical microscopic properties of materials, by utilizing a quantum mechanical phenomenon, named Nuclear Magnetic Resonance (NMR), in which a system of spins, placed in a magnetic field resonantly absorb energy, when applied with a certain frequency.

A nucleus can experience NMR only if its nuclear spin I does not vanish, i.e., the nucleus has at least one unpaired nucleon. Examples of non-zero spin nuclei frequently used in MRI include $^1H$ (I=1/2), $^2H$ (I=1), $^{23}Na$ (I=3/2), etc. When placed in a magnetic field, a nucleus having a spin I is allowed to be in a discrete set of energy levels, the number of which is determined by I, and the separation of which is determined by the gyromagnetic ratio of the nucleus and by the magnetic field. Under the influence of a small perturbation, manifested as a radiofrequency magnetic field, which rotates about the direction of a primary static magnetic field, the nucleus has a time dependent probability to experience a transition from one energy level to another. With a specific frequency of the rotating magnetic field, the transition probability may reach the value of unity. Hence at certain times, a transition is forced on the nucleus, eventhough the rotating magnetic field may be of small magnitude relative to the primary magnetic field. For an ensemble of spin I nuclei the transitions are realized through a change in the overall magnetization.

Once a change in the magnetization occurs, a system of spins tends to restore its magnetization longitudinal equilibrium value, by the thermodynamic principle of minimal energy. The time constant which control the elapsed time for the system to return to the equilibrium value is called "spin-lattice relaxation time" or "longitudinal relaxation time" and is denoted $T_1$. An additional time constant, $T_2$ ($\leq T_1$), called "spin-spin relaxation time" or "transverse relaxation time", controls the elapsed time in which the transverse magnetization diminishes, by the principle of maximal entropy. However, inter-molecule interactions and local variations in the value of the static magnetic field, alter the value of $T_2$, to an actual value denoted $T_2^*$.

In MRI, a static magnetic field having a predetermined gradient is applied on an object, thereby creating, at each region of the object, a unique magnetic field. By detecting the NMR signal, knowing the magnetic field gradient, the position of each region of the object can be imaged. Thus, pulse sequences are applied to a subject to generate NMR signals and obtain information therefrom which is subsequently used to reconstruct images of the object. The above mentioned relaxation times and the density distribution of the nuclear spin are properties which vary from one normal tissue to the other and from one diseased tissue to the other. These quantities are therefore responsible for contrast between tissues in various imaging techniques, hence permitting image segmentation.

Although MRI is the non-invasive, in-vivo imaging modality that provides the best anatomical details on the human brain, it was realized by the present inventors that the visualization of the cortical layers is challenging. The present inventors realized that the background art has failed to provide in-vivo imaging modality that enables visualization of cell structures, mainly due to resolution and image contrast limitations. The width of the cortex is about 2-4 mm, the layers width range from 0.2 to 1 mm and typical human imaging resolution is of the order of 1-2 mm. Thus, in order to achieve sufficient resolution that allows identification of the layers, long acquisition time and extremely strong magnets are required to overcome the poor signal to noise ratio. Additionally, MRI detects water and thus is not specific to cell morphology in general and neuronal cell architecture in particular. Furthermore, since the MRI signal along the cortex appears to be iso-intense, the background art has failed to detect fine structures within the cortex.

Several works have been directed to extreme resolution anatomical magnetic resonance (MR) images of excised cortical tissue and small sections of in-vivo human brain.

High-resolution (0.39×0.39×3.0 mm$^3$) T1-weighted MRI was used to visualize the border between the striate (Brodmann area 17) and extra-striate cortex (Brodmann areas 18 and 19). This was attributed to the heavily myelinated layer IV of area 17 (stria of Gennari) that is less apparent in adjacent regions [Clark et al., "In vivo myeloarchitectonic analysis of human striate and extrastriate cortex using magnetic resonance imaging," 1992 Cereb Cortex, 2(5):417-424]. Other works [Walters et al., 2003, "In vivo identification of human cortical areas using high-resolution MRI: an approach to cerebral structure-function correlation," Proc Natl Acad Sci USA 100(5):2981-2986; and Barbier et al., 2002, "Imaging cortical anatomy by high-resolution MR at 3.0T: detection of the stripe of Gennari in visual area 17," Magn Reson Med 48(4):735-738] showed discrimination of the stria of Gennari was obtained by high resolution T2-weighted MRI, indicating that high resolution MRI is potentially sensitive to the cortical microstructural arrangement and architecture.

The present inventors realized, however, that since these experiments require strong magnetic fields (above 7T) and lengthy scanning times, they cannot be the basis for routine, three-dimensional, whole brain, in-vivo protocol that can demonstrate or be sensitive to the cortical architecture.

One attempt was directed to analyze MR signal profiles perpendicular to the cortical strip (cortical profiles) at relatively less high image resolution [Eickhoff et al., supra]. The present inventors realized that the contrast between the layers, as appears in these cortical profiles, is not strong enough to allow a robust segmentation of the layers.

Other approaches tried to enhance the contrast between the layers either by using contrast agents or other MRI contrast mechanisms [Silva et al., 2008, "Detection of cortical laminar architecture using manganese-enhanced MRI," J Neurosci Methods 167(2):246-257; Angenstein et al., 2007, "Manganese-enhanced MRI reveals structural and functional changes in the cortex of Bassoon mutant mice," Cereb Cortex 17(1):28-36].

While conceiving the present invention it was hypothesized that each cortical layer exhibits significant difference in at least one of the physical properties, such that the layers are distinguishable according to these physical properties. More particularly, but not exclusively, the inventors of the present invention found that different areas along the cortex differ in their longitudinal relaxation time properties and that these areas can be zeroed by choosing specific inversion time. Thus, some embodiments of the present invention employ MRI to characterize cortical sub-structures. The present inventors demonstrated that these areas distribute along the cortex in a laminar fashion that resembles the histological appearance of the cortical layers. The width of the inversion recovery layers changes between different cortical regions and was found to be in strong correlation with the histological measures of the cortical layers width.

Before providing a detailed description of various embodiments of the present invention, attention will be given to the advantages and potential applications offered thereby.

The present inventors successfully demonstrated that a laminar pattern of cortical sub-structures can be identified in vivo in a non-invasive manner using MRI. It is recognized that the morphological characteristic of the cortex represents a fingerprint of development, cognitive abilities and indicates on future diseases. The technique of the present embodiments can be employed in many areas including, without limitation, neurobiology, psychology and neurological research. The current knowledge on brain neuro-anatomical organization is from few histological samples that underwent a whole brain cyto-architectonic analysis. Without being bound to any specific theory, it is postulated that these samples do not represent or apply to the entire population. The in-vivo measurement of the present embodiments allows a large population study where inter-subject variability can be assessed and correlated with subject specific cognitive abilities.

As brain function and brain morphology are linked it is postulated that measuring variations in the anatomical organization of the brain can be used to identify functional differences. Additionally, defining which of the cortical sub-structures are affected in disease can improve the understanding of the mechanism of a certain disease and can also provides means for their early detection. For example, it is suggested that mal-development of certain cortical layers in specific regions in Alzheimer's disease, schizophrenia and autism precedes the clinical symptoms of these diseases. The present embodiments successfully provide a technique which can be used to measure, quantify and follow-up these cortical structures in vivo, so as to validate or identify clinical symptoms that predict a development of a certain disease.

In addition, the ability of the present embodiments to perform follow-up studies with MRI allows observing a dynamic change in the cortical pattern during development and in response to skill development in adulthood. The present embodiments can be used for following the morphological manifestation of learning and memory, development of a mental skill, language and other cognitive abilities. A particular advantage of the technique of the present embodiments is that it allows visualization of the cortical lamination patterns in three dimensions and for the whole brain.

The technique of the present embodiments is advantageous since it can be based on standard MRI protocol and scanner setup, using simple image processing procedures. The technique of the present embodiments can, in some aspects of these embodiments, facilitate visualization of cortical lamination patterns of the whole brain in three dimensions. The present inventors discovered that, compared to conventional techniques (e.g., T2-weighted, T2*-weighted, T1-weighted and contrast-enhanced MRI), the inversion recovery technique of the present embodiments provide high contrast that allows a robust identification of cortical structures, particularly, but not exclusively, cortical layers. As demonstrated in the Examples section that follows, high contrast for different parts of the cortex can be achieved by selecting different inversion times for different times. This can be used for constructing a multispectral dataset that allows clustering, preferably with a predetermined number of clusters (e.g., 5 or 6 clusters), based on regional contrast profiles. Such multispectral analysis is found by the present inventors to be unbiased and model-free.

Figure 1:
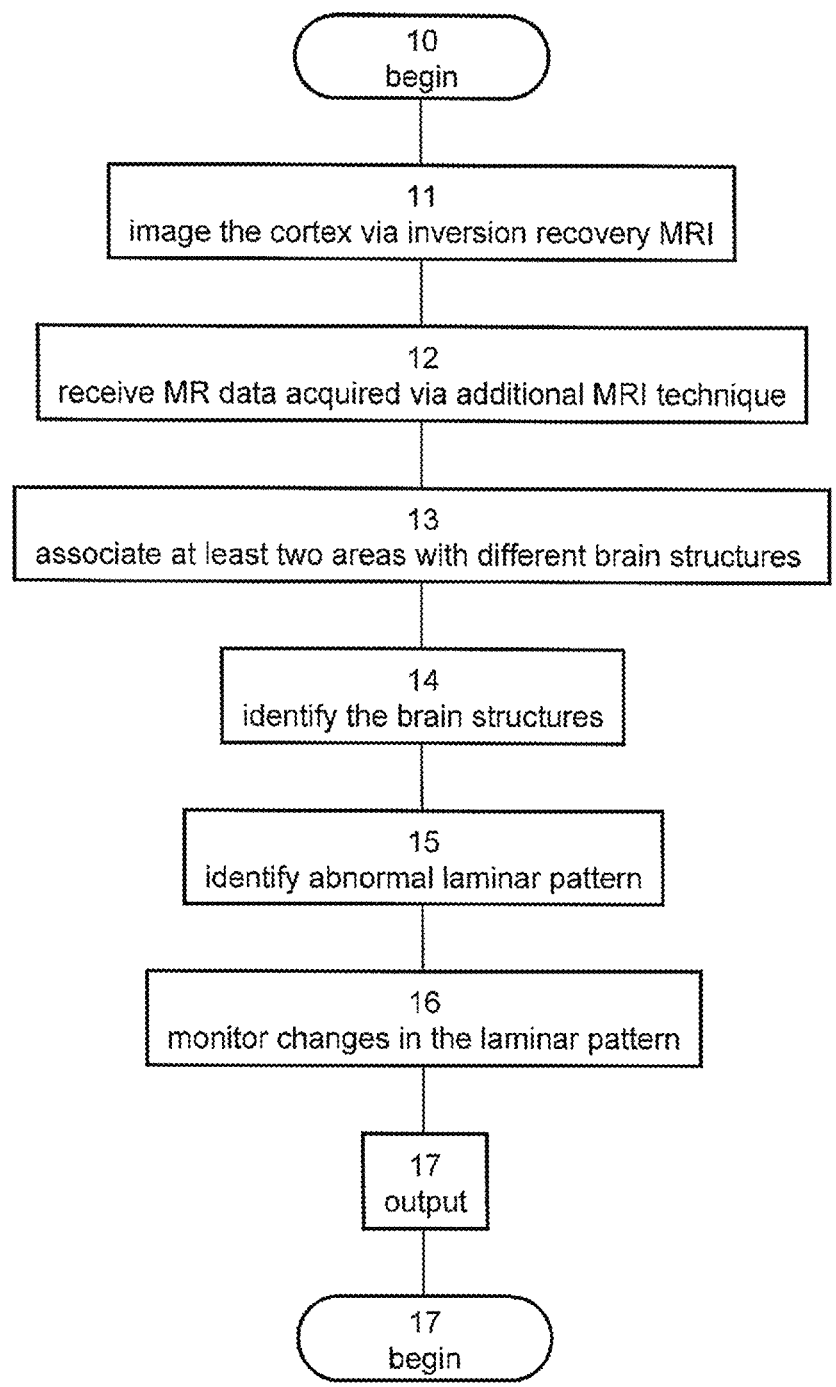

Referring now to the drawings, FIG. 1 is a flowchart diagram of a method suitable for identifying brain structures, according to various exemplary embodiments of the present invention. It is to be understood that, unless otherwise defined, the operations described hereinbelow can be executed either contemporaneously or sequentially in many combinations or orders of execution. Specifically, the ordering of the flowchart diagrams is not to be considered as limiting. For example, two or more operations, appearing in the following description or in the flowchart diagrams in a particular order, can be executed in a different order (e.g., a reverse order) or substantially contemporaneously. Additionally, several operations described below are optional and may not be executed.

The method begins at 10 and optionally and preferably continuous to 11 at which the cortex of the brain is imaged via inversion recovery MRI. Alternatively, inversion recovery MR data can be input to the method from external source. Inversion recovery is a resonance pulse sequence which is traditionally used for measuring the longitudinal relaxation time, $T_1$. The inversion recovery pulse sequences include a 180° RF excitation pulse that inverts the longitudinal spin magnetization, followed by a recovery time TI in which the longitudinal magnetization of the desired spin species recovers, but that of undesired spin species does not. In a preferred embodiment of the present invention, the pulse sequence employed at 11 is such that for each of at least two areas or regions in the cortex, the longitudinal magnetization of the respective area or region is suppressed compared to the longitudinal magnetization of all other areas or regions, wherein each of these areas or regions is characterized by a different characteristic recovery time.

As used herein, "suppressed longitudinal magnetization" means a longitudinal magnetization which is at most 10% or at most 1% of any other longitudinal magnetization in the imaged region.

An area or region in which the longitudinal magnetization is suppressed is referred to herein as a "zeroed" area or region. The terms "zeroed" and "nulled" are used interchangeable throughout this specification.

Suppression of the longitudinal magnetization can be achieved by judicious selection of the recovery time $TI_0$ at which the spins of the respective tissue pass though the zero magnetization point. For a given MRI system and imaging conditions, the recovery times employed according to some embodiments of the present invention are preferably universal, namely the same set of recovery times can be used for all subjects imaged by the given MRI system and imaging conditions.

In some embodiments of the present invention the MRI is such that a white matter (WM) zone is zeroed in terms of its $T_1$, and in some embodiments of the present invention the MRI is such that a cerebrospinal fluid (CSF) zone is zeroed in terms of its $T_1$. This can be done, for example, using the techniques of Hajnal 1992 (Hajnal et al., 1992 "High signal regions in normal white matter shown by heavily T2-weighted CSF nulled IR sequences," J Comput Assist Tomogr 16(4):506-513), Bydder 1998 (Bydder et al., 1998, "MRI: use of the inversion recovery pulse sequence," Clin Radiol 53(3):159-176) and/or Turner 2008 (Turner et al., 2008 "Optimised in vivo visualisation of cortical structures in the human brain at 3 T using IR-TSE," Magn Reson Imaging 26(7):935-942) the contents of which are hereby incorporated by reference.

It was found by the present inventors that at least one or at least two or at least three of the following recovery times can be used: 160 ms, 230 ms, 432 ms, 575 ms, 760 ms, 1080 ms, 1380 ms and 2100 ms, where the recovery times of 160 ms and 2100 ms correspond to WM and CSF, respectively, and the other recovery times correspond to cortical layers I-VI, respectively. These times are particularly useful for a 3T GE scanner, but may also be used in other similar scanners.

The MRI can be of low resolution. In some embodiments a unit voxel size characterizing the resolution is of at least 1 $mm^3$ (e.g., about 1×1×1 $mm^3$) or at least 4 $mm^3$ (e.g., about 1.6×1.6×1.6 $mm^3$) or at least 8 $mm^3$ (e.g., about 2×2×2 $mm^3$).

The method continuous to 13 at which the method associates the zeroed areas or regions with different brain structures. The association can be done by a data processor which receives the inversion recovery MR data and process it to identify the area or region which corresponds to each recovery time.

For example, the inversion recovery MR data can be analyzed by fitting the data to an exponential decay function according to the following formula:

$$M(TI_i)/M_0 = 1 - 2e^{(-TI_i/T_1)},$$

where $M(TI_i)$ is the magnetization at the i-th inversion recovery time $TI_i$ and $M_0$ is the magnetization when the inversion time is 0. The fit is preferably performed pixelwise or voxelwise. Following the fit, each pixel or voxel can be assigned a single $T_1$ value from which the inversion time that zeroed the magnetization of that pixel can be calculated using the relation: $TI_0 = \ln 2 T_1$.

In various exemplary embodiments of the invention the data are analyzed so as to identify 14 the brain structures. Typically, different regions of the cortex are classified so as to identify a laminar pattern. Typically, such analysis includes classification of the pixels or voxels into clusters according to their inversion times. The pixels or voxels can form laminae in the cortex, such that when there is a plurality of clusters, a laminar pattern is identified. The laminar pattern preferably corresponds to the cortical layers of the brain. The classification can also include identification of a WM zone and a CSF zone, in addition to the cortical layers. Typically, the classification extracts from 6 to 8 clusters, where 5 or 6 of the clusters correspond to cortical layers and the other cluster(s) correspond to at least one of the WM and CSF zones.

The classification can be done using any clustering procedure. For example, in an embodiment of the invention, the virtual-dot-com framework described in Yovel Y and Assaf Y., 2007, "Virtual definition of neuronal tissue by cluster analysis of multi-parametric imaging (virtual-dot-com imaging)," Neuroimage 35(1):58-69, the contents of which are hereby incorporated by reference. Other clustering procedures are not excluded from the scope of the present invention. In various exemplary embodiments of the invention the classification is done in three dimensions.

In some embodiments the data are analyzed by fitting data to a multi-exponential signal decay function, e.g.:

$$M(TI_i)/M_0 = \sum_j f_j \cdot \left(1 - 2e^{(-TI_i/T_{1j})}\right),$$

where j=1, 2, . . . , N, $T_{1j}$ is the jth longitudinal relaxation time of the ith inversion recovery time, and $f_j$ is a weight factor satisfying $\Sigma f_j = 1$. Thus, in these embodiments, each pixel can be assigned a set of longitudinal relaxation times. These embodiments are particularly useful when the resolution of the MRI is low. It was found by the present inventors that at low resolution, each pixel or voxel includes more than one $T_1$. Typically, N equals 7 or 8, such that 5 or 6 of the longitudinal relaxation times can be identified as corresponding to cortical layers, one longitudinal relaxation time can be identified as corresponding to CSF and one longitudinal relaxation time can be identified as corresponding to white matter.

The fitting is preferably preceded by a definition of "cortical vectors". Generally, a cortical vector is a vector that lies perpendicularly to the surface of the brain and extends from the white matter to the CSF. Following the definition of a cortical vector, at least some of the pixels or voxels that resides within this vector can undergo a fit to the above multi-exponential signal decay function. Initial guess and upper and lower limits for the analysis can be used to assure convergence. This can include one or more of the followings: (a) the CSF and WM volume fractions can be set to zero at pixels or voxels that are not adjacent to these tissues; and (b) a $T_1$ histogram can be used for estimating an initial $T_1$ for each of the components, which initial $T_1$ can be allowed to vary at predetermined upper and lower bounds (e.g., ±10%). Following the fit, the weighted fraction of each component can be summed from all pixels and a single cortical vector can be created for each surface point.

In some embodiments, the method identifies at least one Brodmann region among the zeroed areas or regions. Brodmann regions or regions that resemble Brodmann regions can be identified by further clustering the pixels or voxels within each lamia in a previously identified laminar pattern Brodmann regions or regions that resemble Brodmann reasons can be identified by clustering the width of the layers that were identified using the inversion recovery MRI per each cortical surface point. In various exemplary embodiments of the invention at least 5 or at least 10 or at least 15 or at least 20 different regions are identified by such further clustering. Some of these regions can be Brodmann regions and some of these regions can resemble Brodmann regions.

At 12 the method optionally receives MR data acquired via an MRI technique other than inversion recovery MRI. The additional MR data can be combined with the inversion recovery data so as to increase the number of parameters that are extracted from the dataset hence to improve the characterization of different regions in the cortex. The present inventors also contemplate embodiments in which the inversion recovery MRI and additional MRI are acquired together using a combined pulse sequence.

Representative examples of suitable MRI techniques other than inversion recovery MRI include, without limitation, diffusion weighted MRI and functional MRI.

Diffusion MRI is a known MRI methodology which is used to study brain anatomy, architecture and pathophysiological condition. A sub-methodology of diffusion MRI, known as diffusion tensor imaging (DTI) provides means to study the diffusion properties of white matter. In the gray matter, due to low resolution and averaging effect DTI in particular and diffusion MRI in general are less informative. The present inventors uncovered that the inversion recovery MRI can be combined with diffusion MRI (a combined pulse sequence) to study and extract the diffusion properties of each cortical layer. The extracted parameters can include diffusivity, orientation (probably dendrite) organization, cellular density and other parameters for each layer. This can be used for characterizing specific neurological and psychiatric diseases where these properties may provide early detection and better means for follow up and assessment of therapeutic intervention.

Functional MRI (fMRI) is an MRI technique that measures alterations in cerebral blood flow and neural activation in response to external stimuli or cognitive tasks. fMRI is based on the observation that changes in local magnetic susceptibility in the brain, within an externally applied magnetic field are associated with focal changes in the magnetic resonance parameters of nearby tissue. Changes in magnetic resonance parameters result in time dependent local image intensity variations. Although these susceptibility variations can be detected using conventional MRI techniques, echoplanar MRI is typically preferred due to its significantly greater temporal resolution. By recording images at a high rate, small susceptibility changes in vivo are observed on physiological time scales with a high degree of reliability. In some embodiments blood oxygen level dependent (BOLD) signal changes are monitored by fMRI. Inversion recovery MRI can be combined with fMRI BOLD acquisition to assess the contribution the fMRI activation of each cortical layer. This allows better physiological monitoring and neuronal circuit analysis of the fMRI BOLD signal and differentiation of the BOLD response into its layer components.

In some embodiments of the present invention, the method proceeds to 15 at which an abnormal laminar pattern is identified. This can be done, for example, by comparing the laminar pattern to known laminar patterns acquired previously and stored in a searchable library. The known laminar patterns can include laminar patterns classified as "normal" and/or laminar patterns classified as "abnormal." Abnormal patterns in the library can also be associated with brain diseases (e.g., Alzheimer's disease, schizophrenia, tourette's syndrome, mania, obsessive compulsive disorder, autism).

Depending on the degree of similarity between the identified pattern and the known pattern, the method can determine whether or not the identified pattern is normal. When the method determines that the identified pattern is abnormal, the method optionally associates the abnormal laminar pattern with a brain disease, according to the association of the known pattern in the library. In some embodiments, the method comprises a stage in which the identified brain disease is treated, for example, by administering therapeutically effective amount of a compound or by any other treatment known in the art.

The method of the present embodiments can also be used for monitoring 16. In these embodiments, the imaging and data analysis is repeated at different times for the same cortex so as to identify changes in the laminar pattern of the cortex. Such changes can be used for assessing brain plasticity, changes in brain function and the like.

At 17 the method outputs the results of the various analyses and assessments to a computer readable medium or displays them on a display device. For example, the method can provides a graphical display of the identified laminar patterns, as demonstrated in the Examples section that follows.

As used herein the term "about" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

Figure 2:
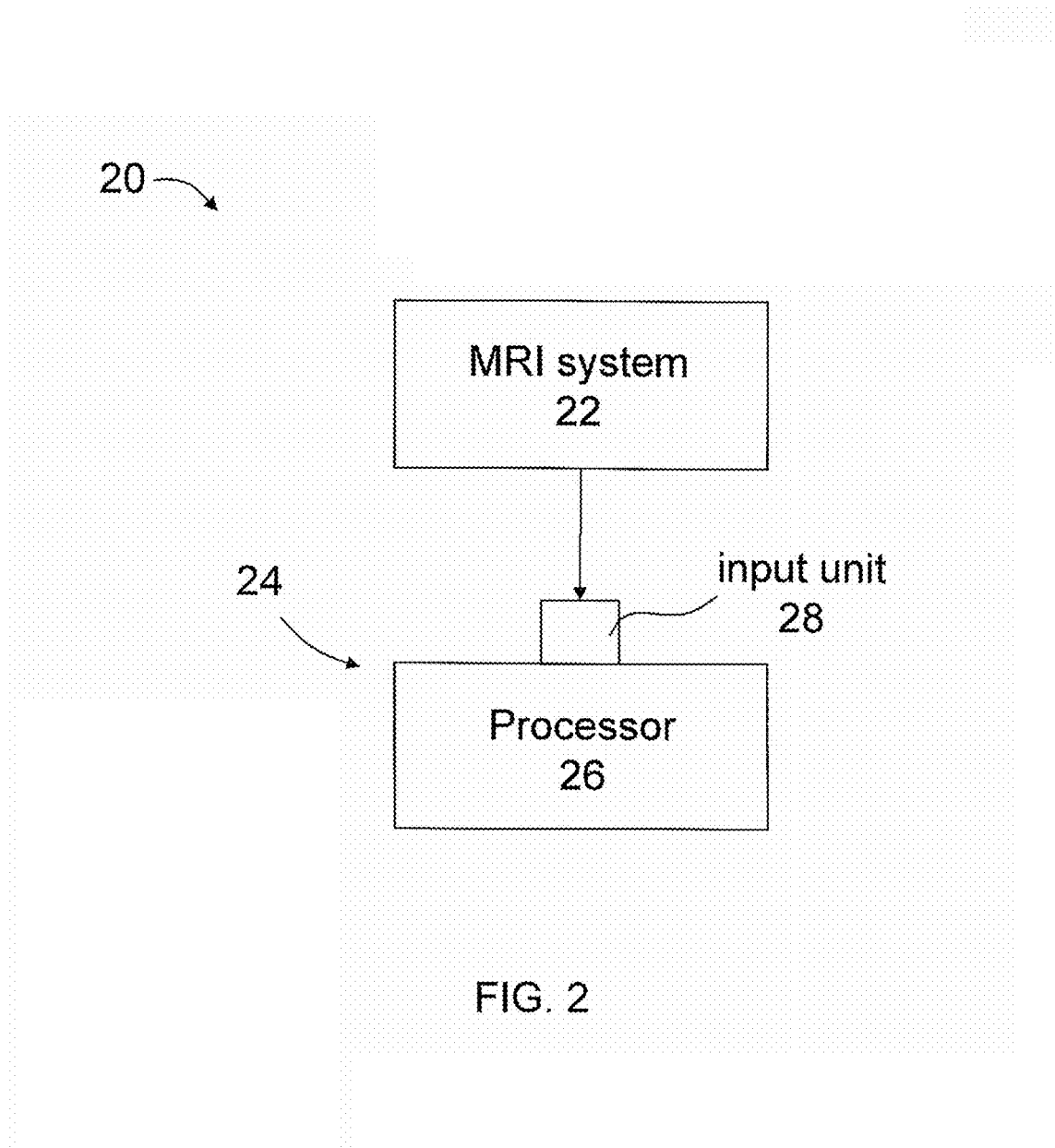

Reference is now made to FIG. 2 which is a schematic illustration of a system 20 for identifying brain structures, according to various exemplary embodiments of the present invention. System 20 comprises an MRI system 22 which images the cortex of the brain via inversion recovery magnetic resonance imaging such that at least two areas of the cortex are zeroed in terms of their longitudinal relaxation times. System 20 further comprises an apparatus 24 which identifies the brain structures. Apparatus 24 comprises a processor 26 which receives the inversion recovery MR data and processes the data such as to associate at least two areas with different brain structures, as further detailed hereinabove. In some embodiments of the present invention the processor performs a multi-exponential signal decay fit, as further detailed hereinabove.

MRI system 22 can be configured for imaging at a resolution characterized by a unit voxel size of at least 1 or at least 4 or at least 8 cubic millimeters. In some embodiments MRI system 22 is configured for imaging via diffusion weighted MRI, and in some embodiments MRI system 22 is configured for imaging via fMRI. The processor can be configured for combining the diffusion weighted MRI or fMRI with the inversion recovery MRI as further detailed hereinabove.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

The present inventors demonstrated that a laminar pattern of cortical sub-structures can be identified in vivo in a non-invasive manner using MRI. The present inventors performed experiments on human and rat brains where the MRI layers were generated from in vivo inversion recovery images according to some embodiments of the present invention. Some experiment were directed to the determination of the relation of the cortical structures to histological layers. These experiments included one-to-one comparison of the inventive in vivo technique with histological cytoarchitectonic analysis.

Methods

Subjects

Humans: 13 healthy subjects were recruited for this study (7 males, 6 females, age between 25-35). Subjects were neurologically and radiologically healthy (i.e., no history of neurological diseases and healthy appearance of clinical MRI protocol). The imaging protocol was approved by Tel Aviv Sourasky Medical Center institutional review board. All subjects signed an informed consent and scanned at the MRI facility of Tel Aviv Sourasky Medical Center.

Rats: 2 male Wistar rats at age of 7 months were used in this study. The Tel Aviv University ethics committee on animal research approved the protocol of this study. During the imaging protocol the rats were anesthetized with ~2% isoflurane (in air). Following the MRI, the rat brains were euthanized and prepared for histology (see below).

Human MRI

MRI was performed on a 3T GE scanner with a 16-channel RF coil and a 50 mT/m gradient system. The protocol included conventional clinical screening sequences: saggital spin-echo T1, axial fast spin-echo T2 and axial fluid-attenuated inversion recovery (FLAIR). The signals were acquired with slice thickness of 4 mm with no gap covering the whole brain. Those sequences were used for screening for radiological abnormalities. The acquisition of the screening protocol lasted for 15 minutes.

In addition to the screening sequences, a series of inversion-recovery fast spin echo images were acquired with the following parameters: TR/TE=6000/8.4 ms with inversion time (TI) varied at the following values: 160, 230, 432, 575, 760, 1080, 1380 and 2100 ms. The 160 and 2100 ms inversion time values were used to produces WM and CSF nulled images, respectively. Whole brain acquisition was done with a matrix of 512×384 (reconstructed to 512×512) with final pixel size of 0.39×0.39 mm$^2$ and slice thickness of 3 mm covering the entire brain. The total acquisition time for the IR-MRI data was around 30 minutes.

In addition to the screening and IR datasets, conventional T1-SPGR was acquired at 1×1×1 mm$^3$ resolutions. The total duration of the MRI protocol was 60 minutes.

Rat MRI

MRI was performed on a 7T/30 Bruker scanner with a 400 mT/m gradient system. The research protocol was similar to the human one with slight modifications as given below.

The inversion times (TI) were varied for each experiment at the following values: 480, 730, 820, 860, 920, 990, 1080 ms and 2700 ms. Image resolution was 256×192 (reconstructed to 256×256) with final pixel size of 0.1×0.1 mm² and slice thickness of 0.4 mm. The total acquisition time for the IR-MRI data set was around 1 hour.

Image Analysis

T1 analysis was done on a pixel-by-pixel basis by fitting of the entire inversion recovery dataset to an exponential decay function according to the following formula:

$$M(TI_i)/M_0 = 1 - 2e^{(-TI_i/T1)},$$

where $M(TI_i)$ is the magnetization at the i-th inversion time and $M_0$ is the magnetization when the inversion time is 0. Following successful fitting, each pixel was assigned a single T1 value from which the inversion time that zeroed the magnetization of the pixel was calculated using the relation: $TI_0 = \ln 2 T1$.

Visualization of the lamination structure from the inversion recovery images was done according to the virtual-dot-com framework [Yovel Y and Assaf Y., supra]. Briefly, following the co-registration (to correct for head movements), the cortex was automatically segmented (based on the SPGR, FLAIR and white matter zeroed IR images). On the segmented cortex basic contrast enhancement were used in order to exclude outlier pixels thus stretching the dynamic range of the image. Next a cluster analysis based on the multi-parametric data was performed as follows: (i) data were normalized to create a uniform scale between the different imaging methods, (ii) data were transforming into a principle component analysis (PCA) space to increase the variance, and (iii) k-means clustering algorithm was employed. The number of k-cluster was set to 5 or 6 according to the results of the Gaussian mixture analysis.

Histology

The rat brains were extracted and fixed with formalin 4% following which the brains were washed with flowing water, dehydrated with a graded series of ethanol (70%, 96%, and 100%) and chloroform until it sank to the bottom of the test tube. Thereafter, the brains were embedded in a paraffin solution (Merck, Ney Jersey, USA) for a few days for hardening. Next, the whole brain was cut into sections of 20 μm with a cryostat microtome (Leica Microsystems SM2500, Germany). The sections were collected over gelatin slides, and post fixed with a solution of sodium phosphoric acid and formalin 37% for a period of two days. A deparaffinization phase was executed by Xylol and a down graded series of ethanol (100%, 96% and 70%) subsequently sections were washed twice with distilled water for 15 minutes.

Pretreatment for cyto-architecture staining was performed by placing the slides in formic acid 4% for three hours and then staining them overnight in a mixed solution of formic acid, double distilled water (DDW), and hydrogen peroxide. Thereafter the slides were washed with DDW a few times. For the silver staining, the slides were stained with a mixture of ammonium nitrate, silver nitrate, tungstosillicic acid (Merck, N.J., USA) [Merker B., 1983, "Silver staining of cell bodies by means of physical development," J Neurosci Methods 9(3):235-241], and formalin 37%, and DW for 20-30 minutes at room temperature. After the silver shade was achieved, the slides were rinsed with acetic unhydrate 1% for 5 minutes to stop the silver staining.

The cyto-architecture images of the whole brain were scanned with a stereotaxic microscope (V12 Lumar, Zeiss, Germany).

Results

Figure 3A:
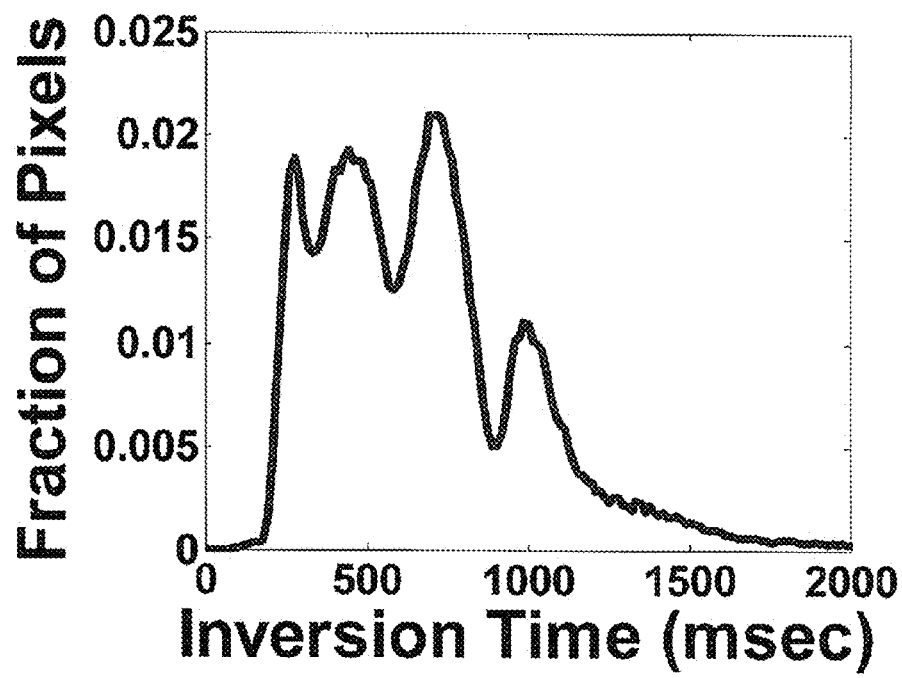

FIG. 3A shows a histogram of the inversion time ($TI_0$) distribution across the entire cortex of a representative subject. As shown, at least 5 distinguishable peaks are identifiable in the histogram. These are centered at 280, 470, 760, 1080 and 1320 ms. Gaussian mixture analysis revealed that the histogram can be characterized with 5-6 distinct Gaussians. This demonstrates that the inversion recovery MRI of the present embodiments allows segmentation of the cortex into sub-structures.

Figure 3B:
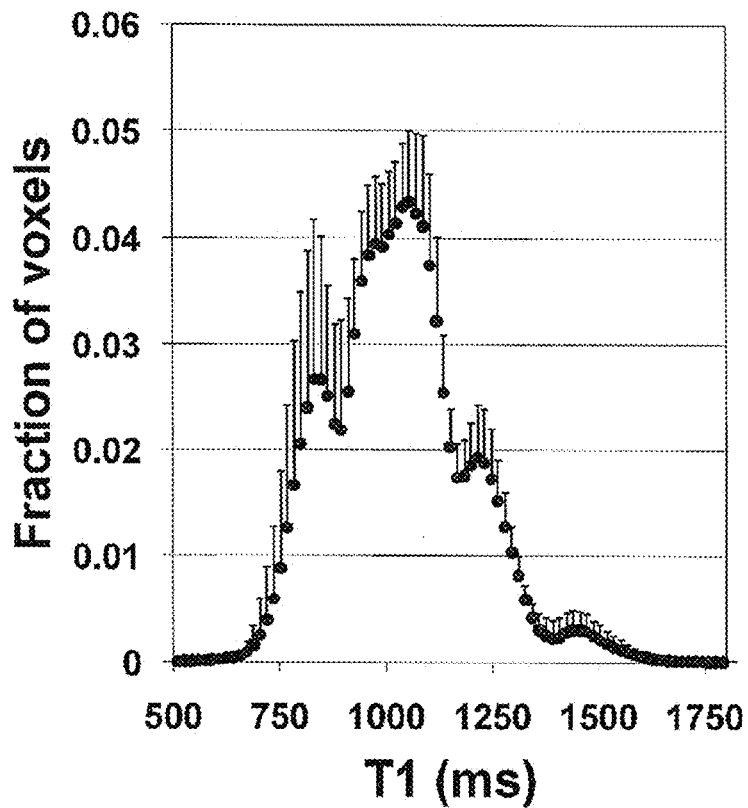

FIG. 3B shows histogram of the longitudinal relaxation time (T1) distribution across the entire cortex averaged for 6 subjects. At least 5 distinguishable peaks are identifiable. These are centered at 830, 960, 1096, 1220 and 1540 ms. Gaussian mixture analysis revealed that the histogram can be characterized with 5-6 distinct Gaussians. The error-bars in FIG. 3B represent standard deviations. The T1 values of the clusters are provided in Table 1, below.

TABLE 1

| Cluster | T1 (ms) |
| --- | --- |
| 1 | 1272 ± 39 |
| 2 | 1139 ± 41 |
| 3 | 1039 ± 49 |
| 4 | 956 ± 61 |
| 5 | 862 ± 65 |

Figure 3C:
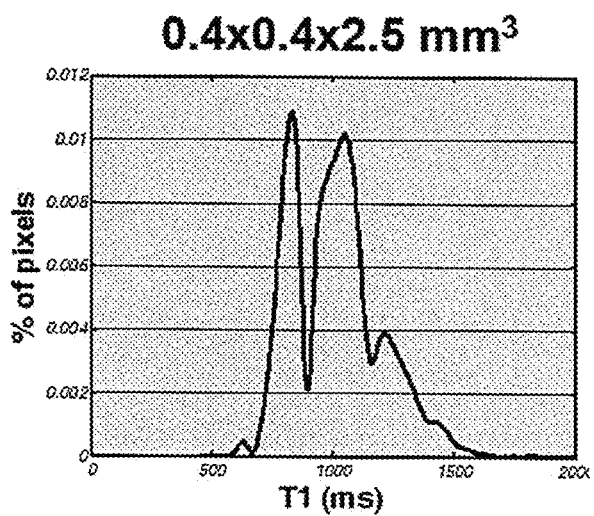
Figure 3D:
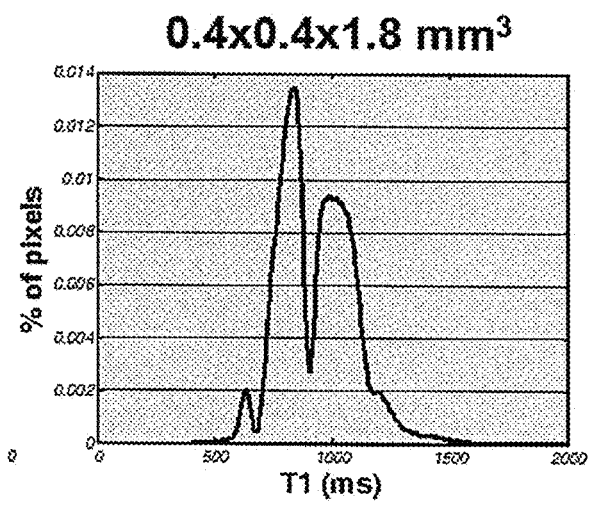
Figure 3E:
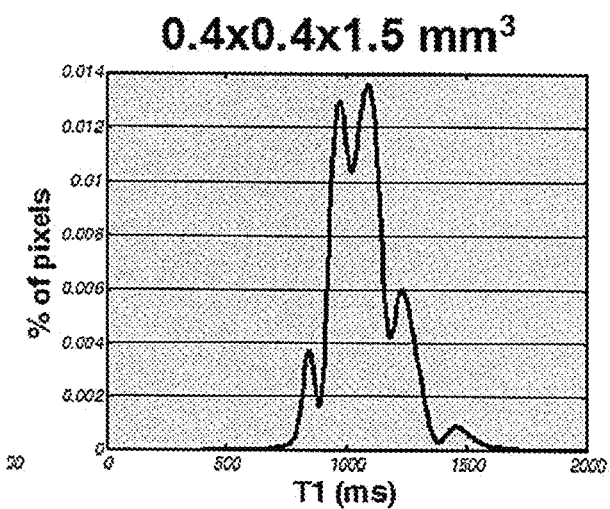

This observation was repeated in all 13 human subjects that were studied. FIGS. 3C-E show histograms of the longitudinal relaxation time distribution across the entire cortex at three different resolutions: (slice thicknesses of 2.5 mm, 1.8 mm and 1.5 mm, respectively). At least 5 distinguishable are identifiable at similar locations in the different resolutions. Although there are some variations between the histograms, FIGS. 3C-E demonstrate that the T1 characteristics are resolution independent and therefore represent true feature of the cortex. The fact that there are variations between the histograms can be attributed to different partial volume effect due to the different resolutions and/or different sampling of the cortex as each one represents a different subject.

The above observation was also repeated in the rat brain experiments, excluding the possibility that it stems from voxel partial volume effects. Therefore, the T1 histogram analysis reveals that a certain inversion recovery times can be defined to zero the signal of specific sub-structure of the cortex.

Similar analysis on the CSF and white matter regions yields that those can be characterized by a much narrower distribution containing 1-2 distinct distributions that do not overlap with the gray matter distribution. Per gray matter T1 cluster, a certain inversion time $TI_0$ was defined so that the majority of pixels belonging to this cluster had a zero or close to zero signal. FIGS. 4A-I show an inversion recovery MR images taken in specific inversion times that zeros or nulls the signal of each of the components shown in FIG. 3.

FIGS. 4A-C are SPGR-T1 (FIG. 4A), FLAIR (FIG. 4B) and inversion recovery (FIG. 4C) images. The inversion time in FIG. 4C was selected to zero the white matter signal. In each of FIGS. 4A-C The border of the cortex as obtained by a multi-spectral analysis is delineated by a contour. As shown, this in this technique that partial volume of the segmented cortex with CSF and white matter can be minimal.

FIGS. 4D-H are a series of inversion recovery images taken at the following inversion times: 280 ms (FIG. 4D), 470 ms (FIG. 4E), 760 ms (FIG. 4F), 1080 ms (FIG. 4G) and 1320 ms (FIG. 4H). The band of nulled signal is marked on FIGS. 4D-H by arrows. As shown, in each inversion time, the band or cortex lamina of zeroed signal moves along the cortex. The collection of all laminae reveals a laminar pattern along the cortex. As $TI_0$ increases, the zeroed lamina of cortical signal moves along the cortex until reaching it boundaries.

The different inversion recovery images can be regarded as a multi-dimensional dataset. FIG. 4I shows results of multi-spectral cluster analysis of this dataset, where regions of the cortex are classified according to their inversion recovery times. A laminar pattern is vivid. Although FIG. 4I is two-dimensional, the cluster analysis was performed in three dimensions. Further, although FIG. 4I shows a portion of the cortex, the analysis was performed for the entire cortex.

FIGS. 4A-I demonstrate that the inversion recovery MRI of the present embodiments allows visualization and quantification of cortical structures.

FIGS. 9A-E shows inversion recovery images at different inversion times at the border between Brodmann area's 17 and 18. In this experiment, the inversion times were chosen to fit the peaks of the multi-Gaussian $T_1$ histogram suggesting that at each inversion times a certain component of cortex signal is zeroed. In the inversion times range of 575-760 ms, which zeroed most of the cortex signal, there is a bright signal band within area 17 indicating a region with similar $T_1$ characteristics of white matter (see FIG. 9C). This region is believed to represent the stria of Genarri. On the other hand, at inversion time of 230 ms, where most of the white matter signal is zeroed, a signal drop at the same region is observed (see FIG. 9B). These observations are manifested in a cluster analysis of the multi inversion time images where a specific cluster that represents the stria of Genarri is present mostly within the territory of area 17. The border between area 17 and 18 is visualized in the clustered and raw data images. Using such segmentation, the $T_1$ histogram of these two regions (the striate and ex-striate cortices) can be computed (see FIG. 9F). The two histograms are different. For area 17, the histogram is shifted towards lower $T_1$ values and vice versa for area 18. Therefore, the histogram and the peak locations represent the underling laminar arrangement of the cortex. In addition, in this histogram, the left peak of area 17 seems to represent the stria of Genarri with the lowest $T_1$ values within the cortex.

An advantage of the presented embodiments is that it can be applied to the whole brain. Thus, the presented embodiments can be used to display a cortical architecture for different regions within the entire cortex.

FIGS. 10A-K show inversion recovery MR images of representative slice out of a 3D dataset taken at different inversion times as in FIG. 9. FIG. 10A is a saggital SPGR T1 weighted image of one representative slice with the cortex borders outlined in red. FIGS. 10B-10G show enlargement of the frontal part of cortex (see yellow rectangle in FIG. 10A) for the SPGR image (FIG. 10B), inversion recovery images with inversion times of 230 ms (FIG. 10C), 432 ms (FIG. 10D), 575 ms (FIG. 10E), 760 ms (FIG. 10F) and 1080 ms (FIG. 10G). The red arrows in (FIGS. 10D-F) show the propagation of the zero band of the inversion recovery image along the cortex as the inversion time increases. FIG. 10H depicts a multispectral analysis of the inversion recovery images where each of the 5 clusters that were found is presented at different color. Note that the width of each cluster varies significantly along the cortex. FIG. 10I depicts enlargement of the frontal regions of clustered image given in FIG. 10H. The corresponding normalized Brodmann area maps of FIG. 10H and FIG. 10I are given in FIGS. 10J and 10K for comparison.

Note that at each inversion recovery MR image a certain lamina of the cortex is zeroed. As the inversion times increases, the zone of low cortical signal moves along the cortex until reaching its boundaries. All zeroed bands, at the different inversion recovery MR images, reveal a laminar pattern along the cortex as indicated by the multispectral cluster analysis (see FIG. 10H, enlarged at FIG. 10I). The cluster analysis of the multispectral inversion recovery datasets allows quantification of the relative thickness of each of the layers as identified by the inversion recovery technique at different regions. FIG. 10H demonstrates that the relative thickness of the different inversion recovery layers varies along different cortical regions. For comparison, FIGS. 10J and 10K depict the normalized Brodmann area map of the same slice. FIGS. 10H and 10J (and their enlargements in FIGS. 10I and 10K) show the resemblance between the cortical regional borders defined by Brodmann map and the changes in laminar appearance as determined by the inversion recovery technique of the present embodiments.

In the following analysis, the Brodmann area map was normalized to each individual subject brain. Ten regions of the frontal lobe (Brodmann areas 4, 6, 8, 9, 10, 11, 44, 45, 46 and 47) were selected for the analysis.

FIG. 11 shows the fraction of inversion recovery layers for the 10 Brodmann areas of the frontal lobe. The regional analysis of the fraction of each inversion recovery layer was achieved following normalization of the Brodmann map to the MRI dataset. The data was averaged over 5 subjects. Error bars represent the standard deviation. Repeated measure ANOVA (5 layers times 10 regions) revealed a significant interaction (layer×region, $F(36,180)=6.6189$, $p<0.000001$) indicating that the regions are separable based on their inversion recovery laminar appearance.

FIG. 12 shows a statistical and regional analysis of the frontal lobe inversion recovery layer fraction. The analysis is shown as a 3D representation of one subject's anatomical T1-SPGR scan with the normalized Brodmann areas of the frontal lobe highlighted in colors with the number of the Brodmann areas indicated in a sphere within the region. The lines indicate a post-hoc pair-wise ANOVA test that was done between two adjacent Brodmann areas' inversion recovery layer volume fractions. White arrows indicate non-significant different (at $p<0.05$), red arrows indicate significant difference that passes a Bonferroni corrected p-value (depending on the number of adjacent comparisons), and pink arrows indicate significant difference when correction for multiple comparison is not accounted for (i.e. $p<0.05$). As shown in FIG. 12 the frontal lobe was successfully segmented according to the present embodiments into 5 areas: area 1 includes Brodmann area 4, area 2 includes Brodmann areas 6 and 8, area 3 includes Brodmann areas 9, 10 and 11, area 4 includes Brodmann areas 44, 45 and 46 and area 5 includes Brodmann area 47.

Of the above analysis, the comparisons between adjacent regions are of particular interest. The statistically significant comparison allows the inversion recovery technique of the present embodiments to outline the border between these regions. Out of the 17 comparison between adjacent Brodmann areas, 11 were statistically significant (9 when correcting for multiple comparisons) as shown in FIG. 12. This analysis demonstrates the ability of the present embodiments to differentiate between anatomical regions.

Better understanding of the biological meaning of the MRI layers has been performed by one-to-one comparison with histology of a rat brain, where the MRI layers, generated from in-vivo inversion recovery images according to some embodiments of the present invention, were compared with histological cyto-architectonic analysis.

FIG. 5A shows cluster analysis of an inversion recovery dataset acquired in-vivo from a rat brain according to the present embodiment, and FIG. 5B shows cyto-architectonic analysis performed on histological sections of the same brain. The result of the cyto-architectonic analysis is superimposed on FIG. 5A. As shown, the changes of the lamination pattern of the MRI the segmentation match borders between cyto-architectonically defined cortical regions. Although the separation between the histological layers II and III with the inversion recovery is not robust, and the border between layers V and IV does not exactly match the histological pattern in some regions, this comparison demonstrates that there is a relation between the histological and MRI layers and that the clustering of the MRI data into 5-6 layers is adequate.

The lamination pattern, as manifested by the width of each of the layer, is the basis for the segmentation of the brain into its neuro-anatomical areas. In the human brain, 47 such areas were defined using cyto-architecture analysis, where each area has a unique lamination pattern. In the following analysis, the map of 47 regions (Brodmann's map) was registered and normalized to the MRI dataset of one subject so as to allow a region wise comparison.

Figure 6A:
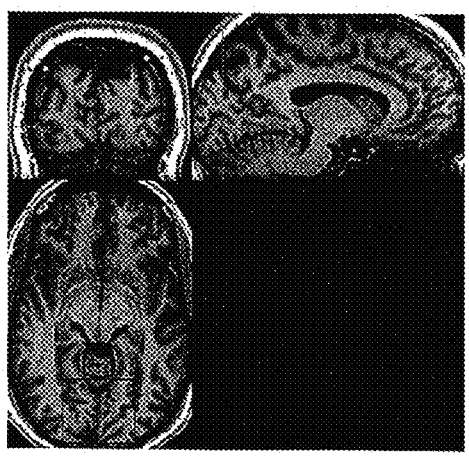
Figure 6B:
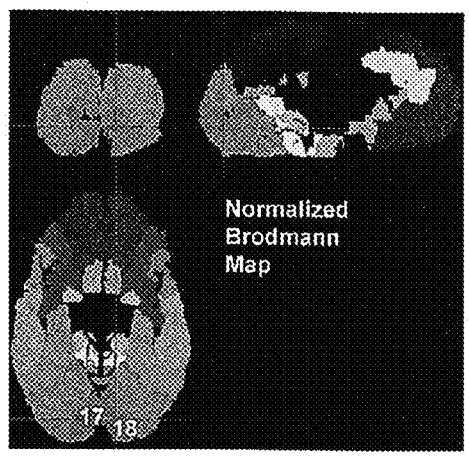
Figure 6C:
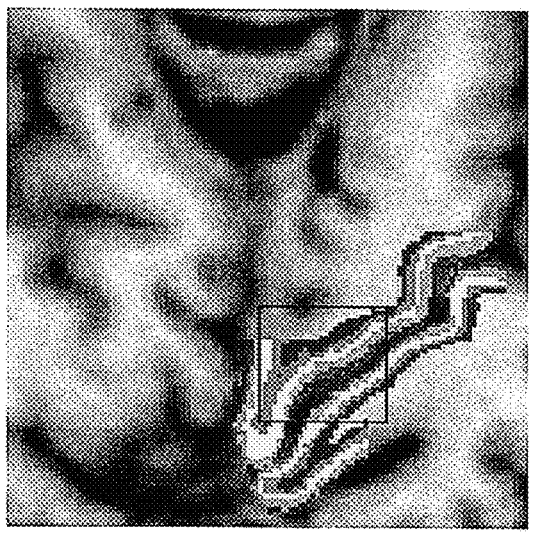
Figure 6D:
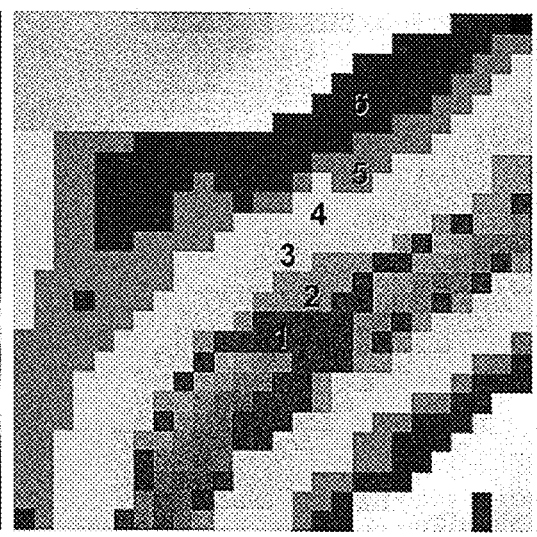

FIGS. 6A-D show the difference in the lamination pattern between areas 17 and 18. FIG. 6A is a SPGR-T1 of a representative volunteer in three views and FIG. 6B is a normalized Brodmann map where each color represents a different Brodmann area. A rectangle on the axial view of FIG. 6A marks a segment of the cortex containing the border between Brodmann's regions 17 and 18. FIG. 6C shows cluster analysis of the inversion recovery data for the marked a segment of FIG. 6A, and FIG. 6D is an enlargement of the rectangle shown in FIG. 6C. The segment that is analyzed in FIG. 6C includes the border between region 17 and 18. The cluster analysis (see FIG. 6D) demonstrates segmentation of the region into six layers and a difference in the laminar pattern in the border. For example, MRI layer 4 is wider (thicker) in area 17 than in area 18, and MRI layer 3 is wider (thicker) in area 18 than in area 17.

FIGS. 7A-B are charts showing a comparison between the lamination pattern as obtained by histology (red bars) and the analysis of the present embodiments (blue bars) for Brodmann areas 17 (FIG. 7A) and 18 (FIG. 7B). Note that the relation between the thicknesses of the layers is preserved in the analysis of the present embodiments.

FIG. 8 shows a comparison between the lamination pattern as obtained by histology (abscissa) and the analysis of the present embodiments (ordinate) for 22 Brodmann areas. The correlation coefficient is $R^2=0.49$ ($p<0.0001$).

Discussion

The present example demonstrate that different areas along the cortex differ in their longitudinal relaxation time properties and that the MR signal of these areas can be zeroed by a judicious selection of the inversion time. The present inventors found that these areas distribute along the cortex in a laminar fashion that resembles the histological appearance of the cortical layers. The width of the inversion recovery layers changes between different cortical regions and was found to be in strong correlation with the histological measures of the cortical layers width. Thus, laminar pattern of cortical structures and sub-structures is identified according to the MRI technique of the present embodiments.

The MRI inversion recovery technique of the present embodiments allows identification of laminar structures within the cortex that has similarities to the cyto-architecture segmentation. The T1 parameter is affected by tissue architecture, cellular density and water/fat ratio. The fact that T1 values become shorter as one moves from the outer parts of the cortex (layers I, II) to its inner parts (layers V, VI) suggests that the tissue become more dense and viscous making the relaxation time longer.

Although cortical architecture has been demonstrated with various MRI methodologies before, the technique of the present embodiments carries several advantages. The technique of the present embodiments based on standard MRI protocol and scanner setup. The technique of the present embodiments also allows visualization of the cortical lamination patterns of the whole brain and in three dimensions. The technique of the present embodiments can be employed using simple image processing procedures. Compared to conventional techniques such as T2-weighted, T2*-weighted, T1-weighted and contrast-enhanced MRI, the technique of the present embodiments provide high contrast that allows a robust identification of the layers. High contrast for different parts of the cortex can be achieved according to the present embodiments with different inversion times, leading to a multi-spectral dataset. The dataset allows clustering, preferably with a predetermined number of clusters (e.g., 5 or 6 clusters), based on the regional contrast profiles. Although the same data is embedded in a T1 calculated map, the multi-spectral analysis is model-free that is not be biased to a predefined model.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:
1. A method of identifying brain structures, comprising:
using magnetic resonance imaging system for imaging the cortex of the brain via inversion recovery magnetic resonance imaging, said imaging comprises applying to the brain energy that is resonantly absorbed in the brain, said energy being applied as a resonance pulse sequence selected such that, for each of at least two areas or regions in the cortex, a longitudinal magnetization of the respective area or region is suppressed compared to a longitudinal magnetization of all other areas or regions, wherein each of these areas or regions is characterized by a different characteristic recovery time;

using an image processor for classifying said at least two areas or regions to a laminar pattern based on characteristic recovery time and associating said at least two areas or regions with different brain structures, thereby identifying brain structures; and graphically displaying said identified laminar patterns on a display.

2. The method of claim 1, wherein said analysis comprises a multi-exponential signal decay fit.

3. The method of claim 2, wherein said fit is performed along a vector perpendicular to the surface of the brain from a white matter region and to a cerebrospinal fluid region.

4. The method of claim 2, wherein said analysis comprises three-dimensional analysis.

5. The method of claim 1, wherein said magnetic resonance imaging is such that at least one of a white matter zone and a cerebrospinal fluid zone is zeroed in terms of its longitudinal relaxation time.

6. The method of claim 1, wherein said at least two areas comprises at least five laminar cortical layers, each corresponding to a different characteristic longitudinal relaxation time.

7. The method of claim 1, further comprising identifying at least one Brodmann region among said at least two areas.

8. The method of claim 1, wherein said magnetic resonance imaging is at a resolution characterized by a unit voxel size of at least 1 cubic millimeter.

9. The method of claim 1, further comprising combining diffusion weighted magnetic resonance imaging with said inversion recovery magnetic resonance imaging.

10. The method of claim 1, further comprising combining functional magnetic resonance imaging with said inversion recovery magnetic resonance imaging.

11. The method of claim 1, further comprising identifying an abnormal laminar pattern in the cortex.

12. The method of claim 11, further comprising associating said abnormal laminar pattern with a brain disease.

13. The method of claim 11, further comprising treating said brain disease.

14. The method of claim 1, further comprising repeating said imaging and said associating at different times for the same cortex so as to identify changes in a laminar pattern of the cortex.

15. The method of claim 14, further comprising assessing brain plasticity based on said changes.

16. The method of claim 14, further comprising assessing changes in brain function based on said changes in said laminar pattern.

17. A system for identifying brain structures, the system comprising;

a magnetic resonance imaging system configured for applying to the brain energy that is resonantly absorbed in the brain to image the cortex of the brain via inversion recovery magnetic resonance imaging, said energy being applied as a resonance pulse sequence selected such that for each of at least two areas or regions in the cortex, a longitudinal magnetization of the respective area or region is suppressed compared to a longitudinal magnetization of all other areas or regions, wherein each of these areas or regions is characterized by a different characteristic recovery time; and an image processor configured for receiving inversion recovery magnetic resonance data from said magnetic resonance imaging system and processing said data such as to classify said at least two areas to a laminar pattern based on characteristic recovery time and to associate said at least two areas with different brain structures.

18. The system of claim 17, wherein said magnetic resonance imaging system is configured for imaging the cortex such that at least one of a white matter zone and a cerebrospinal fluid zone is zeroed in terms of its longitudinal relaxation time.

19. The system of claim 17, wherein said magnetic resonance imaging system is configured for imaging at a resolution characterized by a unit voxel size of at least 1 cubic millimeter.

20. The system of claim 17, wherein said magnetic resonance imaging system is configured for imaging via diffusion weighted magnetic resonance imaging and wherein said processor is configured for combining said diffusion weighted magnetic resonance imaging with said inversion recovery magnetic resonance imaging.

21. The system of claim 17, wherein said magnetic resonance imaging system is configured for imaging via functional magnetic resonance imaging and wherein said processor is configured for combining said functional magnetic resonance imaging with said inversion recovery magnetic resonance imaging.

22. The system of claim 17, wherein said processor is configured for performing a multi-exponential signal decay fit.

23. The system of claim 22, wherein said fit is performed along a vector perpendicular to the surface of the brain from a white matter region and to a cerebrospinal fluid region.

24. The system of claim 22, wherein said analysis comprises three-dimensional analysis.

25. The system of claim 17, wherein said at least two areas comprises at least five laminar cortical layers, each corresponding to a different characteristic longitudinal relaxation time.

26. The system of claim 17, wherein said processor is configured for identifying at least one Brodmann region among said at least two areas.

27. The system of claim 17, wherein said inversion recovery magnetic resonance data is characterized by a unit voxel size of at least 1 cubic millimeter.

28. The system of claim 17, wherein said processor is configured for combining diffusion weighted magnetic resonance imaging with said inversion recovery magnetic resonance imaging.

29. The system of claim 17, wherein said processor is configured for combining functional magnetic resonance imaging with said inversion recovery magnetic resonance imaging.

* * * * *